United States Patent [19]

Duvick et al.

[11] Patent Number: 5,798,255
[45] Date of Patent: Aug. 25, 1998

[54] BEAUVERICIN DETOXIFICATION COMPOSITIONS AND METHODS

[75] Inventors: Jon Duvick; Tracy A. Rood, both of Des Moines, Iowa

[73] Assignee: Pioneer Hi-Bred International, Inc., Des Moines, Iowa

[21] Appl. No.: 753,287

[22] Filed: Nov. 22, 1996

[51] Int. Cl.$^6$ .................. C12N 1/12; C12N 1/20
[52] U.S. Cl. .................. 435/252.1; 435/252.5; 435/253.2
[58] Field of Search ............. 435/252.1, 252.5, 435/253.2

[56] References Cited

U.S. PATENT DOCUMENTS

| | | |
|---|---|---|
| 3,997,568 | 12/1976 | Peters et al. |
| 4,004,978 | 1/1977 | McMullen et al. |
| 4,006,265 | 2/1977 | Tamas et al. |
| 4,998,586 | 3/1991 | Toyoda et al. |
| 5,297,625 | 3/1994 | Premuzic et al. |

FOREIGN PATENT DOCUMENTS

| | | |
|---|---|---|
| 387693 | 8/1988 | Austria . |
| 450721 | 10/1991 | European Pat. Off. . |

OTHER PUBLICATIONS

Platter et al (applied & Env. Microbiology vol. 60 No. 10, Oct. 1994 pp. 3894–3896).

He, et al. 1992. "Microbial transformation of deoxynivalenol." *Appl. Environ. Microbiol.* 58: 3857–3863.

Ueno, Y. 1985. "The toxicology of mycotoxins." CRC Critical Reviews Toxicology 14: 99–132.

Bottalico and Visconti. "*Fusarium* species and their mycotoxins in infected cereals in the field and in stored grain".

Kollarczik, et al. 1994. "In vitro transformation of the *Fusarium* mycotoxins deoxynivalenol and zearalenone by the normal gut microflora of pigs." Natural Toxins, 2: 105–110.

Westlake, et al. 1989. "In vitro metabolism of mycotoxins by bacterial, protozoal and ovine ruminal fluid preparations." Animal Feed Sci. Tech. 25: 169–178.

"Mycofix Plus." Published by BIOMIN Ing. Erber KG.

Logrieco, et al. "Occurrence and toxigenicity of *Fusarium proliferatum* from preharvest maize ear rot, and associated mycotoxins, in Italy." 1995.

Logrieo, et al. 1993. "Natural Occurrence of beauvericiin in prehavest *Fusarium subglutinans* infected corn ears in Poland." J. Agric. Food Chem. 41.

Logrieco, et al. 1993. "Occurrence and toxicity of *Fusarium subglutinans* from Peruvian maize." Myopathologia 122: 185–190.

Zhang, et al. 1994. "Detoxification of moniliformin." Weishengwu Xuebao.

*Primary Examiner*—Anthony C. Caputa
*Assistant Examiner*—Mark Navarro
*Attorney, Agent, or Firm*—Pioneer Hi-Bred International, Inc.

[57] ABSTRACT

The present invention provides a bacterial microorganism having the ability to degrade or detoxify beauvericin or derivatives or analogs of beauvericin. The present invention further provides a method for detoxification of plants pre- or post-harvest using microbes having the ability to degrade or detoxify beauvericin or derivatives or analogs of beauvericin.

4 Claims, No Drawings

BEAUVERICIN DETOXIFICATION COMPOSITIONS AND METHODS

TECHNICAL FIELD

The present invention relates generally to the detection and isolation of beauvericin-degrading organisms and to compositions and methods for detoxification or degradation of beauvericin in grain. This method has broad application in agricultural biotechnology and crop agriculture and in the improvement of food grain quality and feed safety.

BACKGROUND OF THE INVENTION

Fungal diseases are common problems in crop agriculture. Many strides have been made against plant diseases as exemplified by the use of hybrid plants, pesticides and unproved agricultural practices. However, as any grower or home gardener can attest, the problems of fungal plant disease continue to cause difficulties in plant cultivation. Thus, there is a continuing need for new methods and materials for solving the problems caused by fungal diseases of plants. These problems can be met through a variety of approaches. For example, the infectious organisms can be controlled through the use of agents that are selectively biocidal for the pathogens. Another method is interference with the mechanism by which the pathogen invades the host crop plant. Yet another method, in the case of pathogens that cause crop losses, is interference with the mechanism by which the pathogen causes injury to the host crop plant. Still another method, in the case of pathogens that produce toxins that are undesirable to mammals or other animals that feed on the crop plants, is interference with toxin production, storage, or activity.

Within the Fusarium sp. are several important pathogens of corn and other cereals in various countries. In corn, Fusarium is known to cause root, stem and ear rot that results in severe crop reduction. The etiology of Fusarium ear mold is poorly understood, although physical damage to the ear and certain environmental conditions can contribute to its occurrence(Nelson PE (1992) "Taxonomy and Biology of *Fusarium moniliforme.*" Mycopathologia 117: 29–36). Fusarium may be isolated from most field grown maize, when no visible mold is present. The relationship between seedling infection and the stalk and ear diseases caused by Fusarium is not clear. Genetic resistance to visible kernel mold has been identified.(Gendloff E, Rossman E, Casale W, Isleib T, Hart P, 1986, "Components of resistance to Fusarium ear rot in field corn." Phytopathology 76: 684–688; Holley RN, Hamilton PB, Goodman MM, 1989, "Evaluation of tropical maize germplasm for resistance to kernel colonization by *Fusarium moniliforme.*" Plant Dis 73: 578–580). The mycotoxins produced by the Fusarium species that infect plants may accumulate in infected plants or in stored grains, presenting serious health consequences for livestock, humans, and other consumers of meat or other food products of such livestock. Fusarium infection has been associated with chronic or acute mycotoxicoses in both farm animals and man (Botallico, et al.). An important mycotoxin that has been found to be produced by certain Fusarium sp. and has been identified in Fusarium infected crops is beauvericin.

Beauvericin is a fungal toxin produced by various Fusarium species, as well as the fungus *Beauveria bassiana*. Beauvericin is a cyclic peptide, with toxic effects on insects as well as both human and murine cell lines. The activity of beauvericin is due to the ionophoric properties of the compound. Beauvericin is capable of forming complexes with alkali metal cations and affects ion transport across cell membranes. In addition, beauvericin has been reported to be one of the most powerful inhibitors of cholesterol acetyltransferase. Beauvericin has also been shown to induce a type of cell death very similar to apoptosis. Circumstantial evidence further indicates that beauvericin acts in concert with other Fusarium toxins to cause additional toxic effects (1).

Beauvericin has been reported to be found at significant levels in corn from Italy, Peru, and Poland (1,2,3). It is likely that beauvericin will also be found in other areas as more studies are completed. Fusarium species are found in virtually all moldy as well as healthy corn. Food safety is an important issue for grain growers. The European Commonwealth is considering imposing limits on various mycotoxin levels of imported grain.

There is a need in the art for novel methods with which beauvericin may be eliminated from a plant or harvested grain. It is considered important by those skilled in the art to continue to develop inventions in order to protect the final consumer of a plant or harvested grain. The present invention provides the reagents and methodologies necessary to ameliorate plants and harvested grains from beauvericin.

SUMMARY OF THE INVENTION

In one embodiment, the present invention provides an organism having the ability to degrade or detoxify beauvericin or a structurally related mycotoxin. The present invention may further include a mutant of the wild-type organism that has the ability to degrade or detoxify beauvericin or a structurally related mycotoxin. The present invention further provides a method for detoxification of plants pre- or post-harvest using a microbe having the ability to degrade or detoxify beauvericin or a structurally related mycotoxin.

DISCLOSURE OF THE INVENTION

The present invention is based on the discovery of an organism having the ability to degrade the mycotoxin beauvericin. The present invention has resulted from a search for a biological means of detoxifying beauvericin and comprises several bacterial species, isolated from moldy wheat and residential compost, capable of growing on beauvericin as a sole carbon source, degrading it partially or completely in the process.

The practice of the present invention will employ, unless otherwise indicated, conventional techniques of botany, microbiology, chemistry, and biochemistry, which are within the skill of the art. Such techniques are explained fully in the literature. See, e.g. J. H. Langenheim and K. V. Thimann, Botany: Plant Biology and Its Relation to Human Affairs (1982) John Wiley; Cell Culture and Somatic Cell Genetics of Plants, Vol. 1 (I. K. Vasil, ed. 1984); R. V. Stanier, J. L. Ingraham, M. L. Wheelis, and P. R. Painter, The Microbial World, (1986) 5th Ed., Prentice-Hall; O. D. Dhringra and J. B. Sinclair, Basic Plant Pathology Methods, (1985) CRC Press; Maniatis, Fritsch & Sambrook, Molecular Cloning: A Laboratory Manual (1982); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); the series in Methods in Enzymology (S. Colowick and N. Kaplan, eds., Academic Press, Inc.); and Current Protocols in Molecular Biology (John Wiley & Sons, Inc. 1996).

In describing the present invention, the following terms will be employed, and are intended to be defined as indicated below.

A microbe is defined as any microorganism (including both eukaryotic and prokaryotic organisms) such as fungi, yeasts, bacteria, actinomycetes, algae and protozoa, as well as other unicellular structures capable of growth in culture.

A beauvericin-producing microbe is any microbe capable of producing the mycotoxin beauvericin or analogs thereof. Such microbes are generally members of the fungal genus Fusarium, as well as recombinantly derived organisms which have been genetically altered to enable them to produce beauvericin or analogues thereof.

By degrading beauvericin, having the ability to degrade beauvericin, is meant any modification or ability to make any modification to the beauvericin molecule or a structurally related molecule that causes a decrease in or loss of its toxic activity. Such a change can comprise cleavage of any of the bonds, oxidation, reduction, the addition or deletion of a chemical moiety, or any other change that affects the activity of the molecule. Furthermore, chemically altered beauvericin may be isolated from cultures of microbes that produce an enzyme of this invention, such as by growing the organisms on media containing radioactively-labeled beauvericin, tracing the label, and isolating the degraded toxin for further study. The degraded beauvericin may be compared to the active compound for its phytotoxicity or mammalian toxicity in known sensitive species, such as porcines.

By structurally related mycotoxin is meant any mycotoxin having a chemical structure related to a beauvericin or analog of beauvericin, as well as other mycotoxins having similar chemical structures that would be expected to de detoxified by activity of the beauvericin degradative enzymes.

Harvested grain is defined as any form of grain which has been somehow removed from the environment in which it was grown. For example, harvested grain may comprise ear corn, or corn kernels, for example. Harvested grain may further comprise that in storage or that being processed. Processed grain is grain that has been through some form of processing and will be used in the production of food for human consumption or will be used as animal feed ("feed grain").

Within this application, plant refers to a photosynthetic organism including but not limited to an algae, moss, fern, gymnosperm, or angiosperm. Preferably, said plant is one from which feed grain (preferably for human or animal consumption) may be harvested ("harvested grain"). Most preferably, said plant includes any variety of corn (maize), wheat, sorgum, rice and barley.

A mature plant is defined as a plant in which normal development of all vegetative and reproductive organs has occurred.

A plant cell includes any cell derived from a plant, including callus as well as protoplasts, and embryonic and gametic cells.

The present invention comprises a methodology for the isolation of a microorganism having the ability to degrade beauvericin or a structurally related mycotoxin, a microorganism having the ability to degrade beauvericin or a structurally related mycotoxin, and a methodology for degradation of beauvericin or a structurally related mycotoxin on a plant in the field as well as on harvested grain. Said microorganism may include but is not limited to bacteria and fungi. In order to isolate said microorganism having the ability to degrade beauvericin or a structurally related mycotoxin, an assay was developed in which a microorganism is initially isolated from a source material. Said source material may comprise any plant or plant-associated material including but not limited to any green tissue such as the stalk, leaf, ear, or kernel. Plant-associated material may include but is not limited to soil in close approximation to the plant. Said microorganism is then cultured in media having beauvericin as the sole carbon source. The media is then observed for the disappearance of the beauvericin crystals that are initially present in said media prior to culturing said microorganism in said media. The disappearance of said crystals is understood to indicate that said microroganism in said culture has the ability to degrade beauvericin. The assay is termed a "crystal disappearance" assay.

To test the ability of said microorganism isolated by the above-described methodology to degrade or detoxify beauvericin or a structurally related mycotoxin on a plant, a mature plant is inoculated with a beauvericin-producing organism and then treated with an appropriate amount of bacteria having the ability to degrade or detoxify beauvericin or its derivatives or analogs. The treatment may comprise application of a composition comprising an efficacious amount of an organism having the ability to degrade beauvericin to said plant whereby the beauvericin present is degraded. Preferably, said application consists of topically applying said composition upon the tissues of said plant, such that beauvericin upon said tissues is degraded.

Alternatively, said plant may be treated with said organism following harvest (treatment of harvested grain). An important utility for the present invention is the detoxification of zearalenone present in grain following harvest. A suitable feed material or "sample" is spiked with a known amount of mycotoxin delivered in a suitable solvent, preferably ethanol, at an appropriate rate, preferably one ml solvent per gram, followed by sufficient mixing to distribute said mycotoxin throughout said material. A control sample preferably receives solvent only. The final concentration of said mycotoxin is preferably between 0.1 and 1.0 mg per gram of feed material. The sample may then be air-dried to remove excess solvent. The sample is next innoculated with $10^5$–$10^7$ colony forming untis (cfu)/g of log-phase cells of a microorganism having the ability to degrade said mycotoxin, at a sufficient rate, preferably one ml cells per gram, followed by sufficient mixing to distribute said cells throughout said sample. A control sample may comprise cells that have been killed by heating, preferably to approximately 80° C. A control sample may further comprise cells of a microorganism that is not able to degrade said mycotoxin. Said samples are then placed into a container, said container is closed and incubated for a sufficient period of time at an appropriate temperature. Said period of time is preferably within the range of one day to two weeks and said temperature is preferably room temperature or approximately 28° C. Following incubation, the contents of said container is extracted in a suitable organic solvent (or organic aqueous mixture) for recovering said mycotoxin. The resulting extract is then concentrated and subjected to qualitative and quantitative analysis for the presence of said mycotoxin. The amount of said mycotoxin detected in said extract is then compared to the amount of said mycotoxin detected in said control sample, and the efficacy of removal of said mycotoxin expressed as a percent reduction in the level of said mycotoxin in said experimental extract as compared to the level of said mycotoxin in said control sample. In the instant invention, said mycotoxin is preferably beauvericin. These methodologies allow for the degradation of beauvericin on or within said plant or harvested grain, thus providing improved food grain quality and feed safety.

This invention can be better understood by reference to the following non-limiting examples. It will be appreciated by those skilled in the art that other embodiments of the invention may be practiced without departing from the spirit and the scope of the invention as herein disclosed and claimed.

EXAMPLE I

ISOLATION OF BACTERIA THAT DEGRADE BEAUVERICIN

Various sources of plant material that were likely to naturally contain beauvericin were collected as source material for screening. Wheat kernels infested with *Fusarium graminearum* (*F. graminearum*; 140 independent samples) were obtained from a Pioneer Hi-Bred International, Inc. ("Pioneer") wheat breeding station in Indiana. Silage samples were obtained from the Microbial Genetics division of Pioneer and compost samples from local residences (126 independent samples total).

The metabolism of beauvericin was measured using a crystal disappearance assay. Microbes were washed from the source material by placing a small amount in a seven milliliter Falcon tube and adding one to two milliliters sterile distilled water (producing "wash fluid"). Maize kernels were split with a razor blade and one to two kernels were used. Tubes were capped and shaken for one to three hours at room temperature. Beauvericin (Sigma Cat. No. B7510) was prepared as a suspension in mineral salts medium, and was utilized as the sole carbon source. The beauvericin concentration utilized includes but is not limited to 0.75–1.0 milligrams/milliliter in mineral salts medium. The mineral salts medium was prepared by combination of reagents including but not limited to 1.0 g/L ammonium sulfate, 1.0 g/L sodium chloride, 1.0 g/L potassium phosphate, dibasic, 0.2 g/L magnesium sulfate. Sterilization of the solution was accomplished by filtration through a 0.2 micron filter, although various methods for sterilization are available to those skilled in the art. 100 microliters of beauvericin/mineral salts suspension medium was added to each well of a microtiter plate (96 well plate). One microliter of fresh wash fluid was added to each well. Control wells received one microliter of water. After two weeks, one microliter from each well was transferred to a new microtiter plate containing 100 microliters of beauvericin/mineral salts medium. The transfer was then repeated four weeks later. After six weeks, wells were scored for partial disappearance of beauvericin crystals. Typically, the small crystals had been solubilized and metabolized, and only the very largest beauvericin crystals remained. This effect was visualized using an inverted microscope or by examining the plate visually from the underside.

The instant invention comprises a biologically pure culture of a microorganism responsible for beauvericin degradation. Said microorganism was isolated using the following procedure. One microliter was taken from positive wells and added to one milliliter of sterile water. Several ten-fold dilutions were made in sterile water, and 100 microliters from each dilution were plated and spread on YDP agar plates. YDP agar plates were prepared by combination of 10 grams yeast extract (Difco), 20 g Bacto peptone, 0.5 g dextrose, 15 g Bacto agar in water followed by sterilization by autoclaving. From these mixture culture spread plates, individual colonies were streaked for isolation on new YDP plates. An effort was made to choose at least one of every type of bacteria represented on the spread plates. Each bacterium was used to make a dilute suspension in sterile water, and one microliter of this suspension was used to inoculate microtiter wells containing beauvericin in mineral salts as described above.

Initial characterization of bacteria was performed by Gram staining samples. More definitive identification was performed using a combination of techniques. Streak plates of individual bacterial colonies were sent to Microbe Inotech Laboratories, Inc. (St. Louis, Mo.) for tentative identification. The analysis included comparison of bacterial fatty acid methyl esters with Aerobe and Clinical Aerobe databases, and Biolog™ substrate utilization comparison with a Gram positive database. Results of such tests have identified three species of Gram negative or Gram variable *Nocardia globulera*, *Rhodococcus fascians*, and *Bacillus sphaericus* and is demonstrated below in Table I. These cultures were deposited with the American Type Culture Collection (ATCC; 12301 Parklawn Drive, Rockville, Md. 20852 U.S.A.) on Oct. 15, 1996 in accordance with the Budapest Treaty on the International Recognition of the Deposit of Microorganisms for the Purposes of Patent Procedure.

TABLE 1

Microbial isolates having the ability to degrade beuavericin

| ATCC Number | Name | Tentative Identification | Source |
|---|---|---|---|
| 55850 | BEA(2)2904.G4 | *Nocardia globulera* or *Rhodococcus fascians* | Wheat kernels infested with *F. graminearum* |
| 55849 | BEA(1)2904.A12 | *Nocardia globulera* or *Rhodococcus fascians* | Wheat kernels infested with *F. graminearum* |
| 55848 | BEA(1)2905.D1 | *Nocardia globulera* or *Bacillus sphaericus* | Wheat kernels infested with *F. graminearum* |
| 55847 | BEA(1)2904.B11 | *Nocardia globulera* or *Rhodoeoccus erythropolis* | Wheat kernels infested with *F. graminearum* |

EXAMPLE II

TREATMENT OF BEAUVERICIN-CONTAMINATED CORN

A. Treatment of contaminated corn in the field

To test the ability of the bacteria isolated by the above-described methodology to degrade or detoxify beauvericin or its derivatives or analogs on maize, mature plants are inoculated with a beauvericin-producing Fusarium sp. and then treated with an appropriate amount of bacteria having the ability to degrade or detoxify beauvericin or its derivatives or analogs. The treatment consists of topically applying a composition comprising an efficacious amount of bacteria onto the tissues of the maize plant such that beauvericin, including any derivatives or analogs of beauvericin, is partially or completely degraded or detoxified.

B. Treatment of contaminated corn after harvest.

A one to ten gram sample of cracked corn is combined or "spiked" with a known amount of beauvericin in ethanol at a concentration of one gram beauvericin per ml of ethanol, followed by mixing to distribute the beauvericin throughout the mixture. A control sample or samples are mixed with solvent alone. The sample is then air-dried to remove excess solvent. The samples are then inoculated with $10^6$ cfu/g of log-phase cells of a microorganism having the ability to degrade beauvericin, designated BEA(2)2904.G4 (deposited with the ATCC under accession number ATCC 55850) at a rate of one ml cells per gram, and mixed well to distribute said cells within said sample. Controls are mixed with either cells of said microorganism [designated BEA(2)2904.G4, deposited with the ATCC under ATCC accession number 55850] that have been heated to 80° C., such that said cells are non-viable or with cells of a microorganism that does not have the ability to degrade beauvericin. Said mixture is placed in a container, which is then closed and incubated for two weeks at room temperature. At the end of the incubation period, the container is opened, and the entire contents extracted in a suitable organic solvent to recover the beauvericin. The extract is concentrated and subjected to qualitative and quantitative analysis for detection of beauvericin. The amount of beauvericin is determined and compared to controls. The efficacy of removal of beauvericin is determined by comparison of the percent reduction (if any) of the amount of beauvericin in the sample comprising the micoorganism having the ability to degrade beauvericin to the reduction of the amount of beauvericin present in said control sample. Microorganisms designated BEA(1) 2904.A12 (ATCC accession number 55849), BEA(1) 2905.D1 (ATCC accession number 55848), or BEA(1) 2904.B11 (ATCC accession number 55847) are also able to degrade beauvericin, and may be utilized for the above-described purpose.

While a preferred form of the invention has been shown in the drawings and described, since variations in the preferred form will be apparent to those skilled in the art, the invention should not be construed as limited to the specific form shown and described, but instead is as set forth in the claims.

What is claimed is:

1. An isolated microorganism which is deposited under ATCC accession number 55850.

2. An isolated microorganism which is deposited under ATCC accession number 55849.

3. An isolated microorganism which is deposited under ATCC accession number 55848.

4. An isolated microorganism which is deposited under ATCC accession number 55847.

* * * * *